(12) United States Patent
Honshell et al.

(10) Patent No.: US 11,958,944 B2
(45) Date of Patent: Apr. 16, 2024

(54) POLYESTER-COTTON BLEND TEXTILE RECYCLING PROCESS AND SYSTEM WITH ROTATING HYDROLYSIS REACTOR

(71) Applicant: Hybridworks Chemical, LLC, Kettering, OH (US)

(72) Inventors: James Honshell, Kettering, OH (US); Robert H. Fesmire, Barrington Hills, IL (US)

(73) Assignee: Hybridworks Chemical, LLC, Kettering, OH (US)

( * ) Notice: Subject to any disclaimer, the term of this patent is extended or adjusted under 35 U.S.C. 154(b) by 0 days.

(21) Appl. No.: 18/213,520

(22) Filed: Jun. 23, 2023

(65) Prior Publication Data

US 2023/0416491 A1 Dec. 28, 2023

Related U.S. Application Data

(60) Provisional application No. 63/355,140, filed on Jun. 24, 2022.

(51) Int. Cl.
*C08J 11/14* (2006.01)
*C08J 11/16* (2006.01)

(52) U.S. Cl.
CPC ............... *C08J 11/14* (2013.01); *C08J 11/16* (2013.01)

(58) Field of Classification Search
USPC .......................................................... 521/45
See application file for complete search history.

(56) References Cited

U.S. PATENT DOCUMENTS

| | | |
|---|---|---|
| 4,345,039 A | 8/1982 | Cowan et al. |
| 5,095,145 A | 3/1992 | Rosen |
| 5,236,959 A | 8/1993 | Oakley et al. |
| 5,342,854 A | 8/1994 | Serad |
| 5,395,858 A | 3/1995 | Schwartz, Jr. |
| 5,413,681 A | 5/1995 | Tustin et al. |
| 5,414,113 A | 5/1995 | Broeker et al. |
| 5,473,102 A | 12/1995 | Johnson et al. |
| 5,886,057 A | 3/1999 | Harvie et al. |
| 6,472,557 B1 | 10/2002 | Pell, Jr. et al. |
| 10,322,395 B2 | 6/2019 | Kumar et al. |
| 10,501,599 B2 | 12/2019 | Barla et al. |
| 10,603,651 B2 | 3/2020 | Kumar et al. |
| 11,180,629 B2 | 11/2021 | Barla et al. |
| 11,305,254 B2 | 4/2022 | Kumar et al. |
| 11,370,895 B2 | 6/2022 | Barla et al. |
| 2008/0097120 A1 | 4/2008 | Jermolovicius et al. |
| 2010/0048081 A1 | 2/2010 | Topolkaraev |
| 2011/0172461 A1 | 7/2011 | Rogers |
| 2017/0335513 A1 | 11/2017 | Henriksson et al. |
| 2018/0339957 A1 | 11/2018 | Auras et al. |
| 2020/0157307 A1 | 5/2020 | Guo |
| 2021/0017353 A1 | 1/2021 | Sramek et al. |
| 2021/0079564 A1 | 3/2021 | Klaus-Nietrost et al. |
| 2021/0269969 A1 | 9/2021 | Brelid et al. |
| 2021/0309825 A1 | 10/2021 | Guo |
| 2022/0153674 A1 | 5/2022 | Anderson et al. |

FOREIGN PATENT DOCUMENTS

| | | | |
|---|---|---|---|
| BR | 112021000329 A2 * | 4/2021 | ............ B29B 17/02 |
| BR | 112021000329 A2 | 4/2021 | |
| CN | 101086706 A | 12/2007 | |
| CN | 103613784 A | 5/2014 | |
| EP | 0550979 A2 | 7/1993 | |
| JP | 2009001734 A | 1/2009 | |
| WO | WO 199627045 A1 | 9/1996 | |
| WO | WO 2020126171 A1 | 6/2020 | |
| WO | WO-2020252523 A1 * | 12/2020 | ............ C08B 16/00 |
| WO | WO 2020252523 A1 | 12/2020 | |
| WO | WO 2021115931 A1 | 6/2021 | |
| WO | WO 2021115932 A1 | 6/2021 | |
| WO | WO 2021/211506 A1 | 10/2021 | |

OTHER PUBLICATIONS

BR 112021000329 Machine Translation (Year: 2021).*
WO-2020252523-A1 Machine Translaiton (Year: 2020).*
Palme, Anna et al., *Development of an Efficient Route for Combined Recycling of PET and Cotton from Mixed Fabrics*, Textiles and Clothing Sustainability (2017).
*A New Textiles Economy: Redesigning Fashion's Future*, Ellen MacArthur Foundation (2017).
International Bureau, International Search Report in International Application No. PCT/US 23/26105, dated Jan. 4, 2024.

\* cited by examiner

*Primary Examiner* — Terressa Boykin
(74) *Attorney, Agent, or Firm* — Leydig, Volt, & Mayer, Ltd.

(57) ABSTRACT

A method for processing polyester-cotton blend textile waste includes adding polyester-cotton blend textile waste to a rotating drum of a rotary hydrolysis reactor. Water and a base are added to the rotary hydrolysis reactor and heated. The polyester-cotton blend textile waste is agitated with a plurality of ribs by rotating the inner drum relative to a housing of the rotary hydrolysis reactor to enable the hydrolysis of PET into a TPA and ethylene glycol solution with solid reclaimed cotton free of PET. The TPA and ethylene glycol solution is separated from the solid reclaimed cotton and directed to a hydrolysate recovery vessel. In the hydrolysate recovery vessel the TPA is precipitated and separated from the remaining liquid and the ethylene glycol is then recovered.

20 Claims, 14 Drawing Sheets

POLYESTER-COTTON BLEND TEXTILE RECYCLING PROCESS AND SYSTEM WITH ROTATING HYDROLYSIS REACTOR

CROSS-REFERENCE TO RELATED APPLICATIONS

This patent application claims the benefit of U.S. Provisional Patent Application No. 63/355,140, filed on Jun. 24, 2022, which is incorporated by reference

BACKGROUND OF THE INVENTION

Many millions of tons of textile waste are produced every year. Most of this textile waste ends up in landfills. A large proportion of the textile waste sent to landfills consists of blended fabrics that include both cotton and synthetic polyester material. The polyester portion of these blended fabrics can take up to 200 years to decompose in a landfill. Thus, polyester-cotton blend textile waste has substantial detrimental effects on the environment which can include the release of greenhouse gases and the leaching of toxins and dyes into the surrounding soil and water.

In order to reduce this environmental impact, a number of processes and systems are used to recycle at least some of this textile waste. Most of these processes require mechanically shredding or reducing the textile waste so that these fabrics can be reused as rags, filler and insulating material. Reducing mechanically produces the highest value products when the waste stream is pure, such as 100% polyester fabrics or 100% cotton fabrics. Blended fabrics can also be mechanically reduced; however, the products that those blended fabrics can be used for have much less value. Inherently, the mechanical reduction of all textiles degrades the textiles and the spinning of yarns from shredded textile materials leads to yarns of low quality. As a result, there are limited end products that can be produced economically using mechanically shredded textiles.

Other methods of recycling polyester-cotton blend textile waste have been proposed which involve chemically separating the cotton from the polyester (polyethylene terephthalate or PET). Some such methods use a depolymerization reaction to dissolve the PET fibers and thereby separate the PET from the cotton fibers. The known depolymerization processes are not economically feasible when scaled-up. For example, many such processes focus on recycling the PET, which has a lower value, and the separated cotton is degraded to a cellulosic level which requires reconstitution. Such processes require cost-prohibitive additional steps in order for the cotton to be reusable, otherwise the cotton could be destroyed. In some cases, the cotton is degraded to a cellulosic material that has to be reconstituted in order to make a viscose fiber. Moreover, the recycled PET has limited usage in new products and is primarily used for low value plastic water bottles. Some of these methods produce some PET that is used in lower grade fibers that are used in some textiles. As a result, these processes do not make the most efficient use of the separated cotton and PET.

Other drawbacks with known depolymerization processes for separating polyester and cotton make them unsuitable for use in large scale textile recycling. For example, the processes, and the equipment that would be used in such processes, would require a significant amount of energy, water and chemicals to ensure an effective depolymerization reaction. The energy, water and chemical requirements alone would make such processes costly to operate. Furthermore, the equipment used in such processes is not readily scalable to high-volume recycling operations.

In particular, conventional batch reactors that could be used to perform the depolymerization process have a limited load capacity for solid textile products. Such reactors are also difficult and time-consuming to load and unload with cleaning of the interior needed even after manual removal of the solid materials. As a result, significant manpower would be necessary in order to operate a batch reactor in this type of application. Such reactors would also require a relatively long run time because of the need to increase temperature in order to effectively separate the PET and cotton. More water is also needed in this type of reactor along with a corresponding increase of chemicals due in large part to the type of stirring and mixing mechanism used in these machines, which is primarily a rotating stirrer or paddle. If water capacity is not high enough the paddles will be hampered by the textiles hanging on the paddles. This causes much increase in costs for water and chemicals as well as labor. Moreover, batch reactors would be difficult to clean, requiring significant time and resources to maintain. The significant production downtime, high operating costs and low production speeds that would be associated with such equipment make their use in large scale textile recycling operations uneconomical.

OBJECTS OF THE INVENTION

In view of the foregoing, a general object of the present invention is to provide a process and system for recycling polyester-cotton blend textiles that is both low-cost to operate and scalable to high-volume production.

Another object of the present invention is to provide a process and system for recycling polyester-cotton blend textiles that requires minimal manpower to operate.

A further object of the present invention is to provide a process and system for recycling polyester-cotton blend textiles that produces high quality end products suitable for versatile reuse.

A related object of the present invention is to provide a process and system for recycling polyester-cotton blend textiles that makes the constituent materials used in blended textiles available for use in 100% cotton products while also making available pure terephthalic acid and ethylene glycol which can be used for making polyester or any other plastics or, with respect to ethylene glycol in particular, coolants, hydraulic fluids and paints.

Another related object of the present invention is provide a process and system for recycling polyester-cotton blend textiles that allows for reclamation of buttons, zippers and other metallic components from garments and melamine buttons.

A further object of the present invention is to provide a process and system for recycling polyester-cotton blend textiles that is energy-efficient.

Another object of the present invention is to provide a process and system for recycling polyester-cotton blend textiles that uses minimal amounts of water and chemicals.

A related object of the present invention is to provide a process and system for recycling polyester-cotton blend textiles that allows for reclamation of the chemicals used as well as clean water.

A further object of the present invention is to provide a process and system for recycling polyester-cotton blend textiles that can be automatically loaded and unloaded quickly and easily.

Other objects and advantages of the invention will become apparent upon reading the following detailed description and upon reference to the drawings. The identified objects are not intended to limit the present invention.

DETAILED DESCRIPTION OF THE INVENTION

Referring to FIGS. 1-4 of the drawings, there are provided schematic diagrams of an exemplary processes and systems for particular use in recycling polyethylene terephthalate (PET)-cotton blend textile materials. Such materials are typically referred to as polyester-cotton blend textiles and are sometimes referred to herein as blended textiles. These blended textiles may take any form and may have any amount of polyester fibers and cotton fibers. In particular, a polyester-cotton blend forms the basis of many textiles or fabric items, e.g., bedding, sheets, towels, and clothing. The proportion of polyester to cotton in such materials is not limited but often will be 50:50, 40:60, or 35:65. The polyester component of a blended textile may be a discrete element including elements as small as a label or decorative component or polyester fibers may be integrated with cotton fibers throughout the textile. In some aspects, the process and system of the present disclosure uses a whole blended textile. In other aspects, the textile is in pieces at the outset. The pieces of blended textile can be prepared using any suitable cutting method (e.g., cutting, shredding, tearing, mechanical shearing, etc.). Thus, it should be understood that the present invention is not limited to any particular type or form of polyester-cotton blend textile.

While the present invention is described in connection with blended textiles, it should be understood that the present invention is not limited to use in recycling blended textiles. For example, textiles or other items, such as plastic bags, made entirely of polyester could also be recycled using the process of the present invention. Accordingly, the present invention is not limited to the recycling of any particular material.

Figure 1:
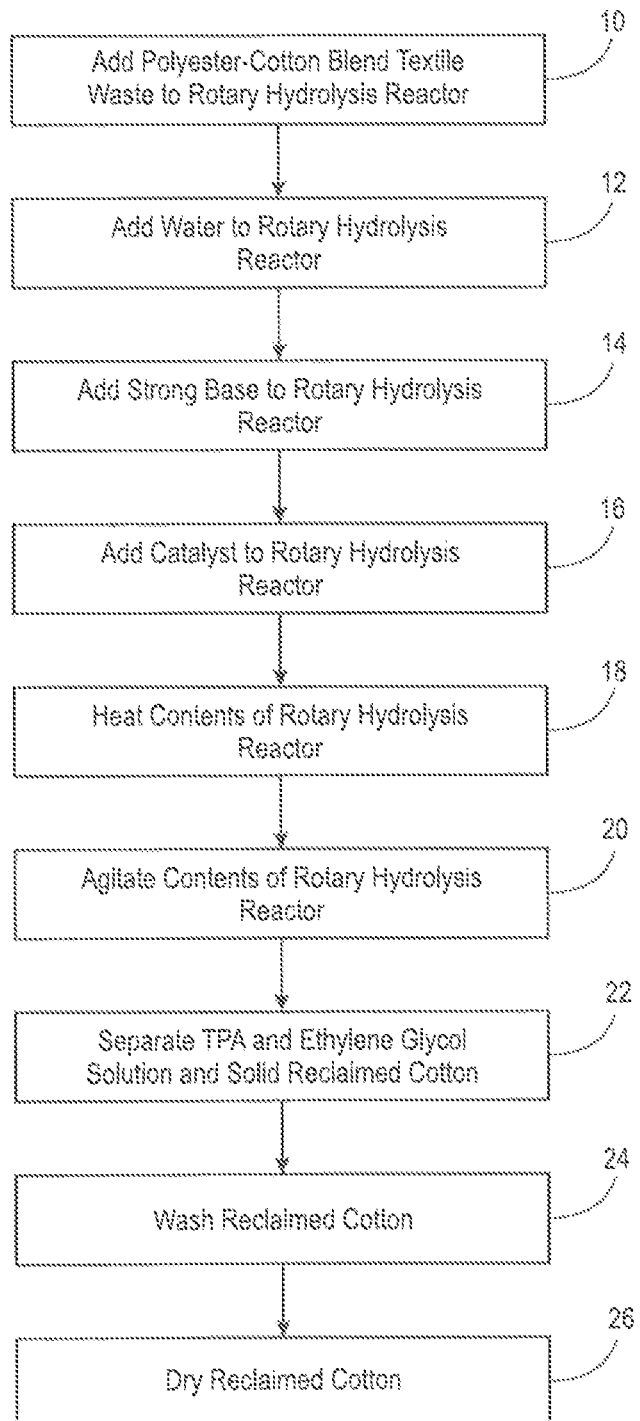
FIG. 1 is a flow diagram showing exemplary steps of a process for recycling polyester-cotton blend textile materials according to the present disclosure.

FIG. 1 is a flow diagram showing exemplary steps of a recycling process according to the present disclosure. The steps of FIG. 1 can be considered a first phase of the process which is completed using a rotating hydrolysis reactor. The illustrated process depolymerizes the PET using a hydrolysis reaction to separate the PET from the cotton in the blended textile materials. It will be appreciated from the following description that not all of the steps included in FIG. 1 are necessary to practice the blended textile recycling process and moreover that the illustrated process steps may be performed in a different order. In a first step 10, polyester-cotton blend textile waste is provided to a rotating hydrolysis reactor. An exemplary rotating hydrolysis reactor that offers several important advantages is shown in FIGS. 5-14 and described in further detail below. While the process is described as being performed on multiple polyester-cotton blend textiles at a time, it should be understood that the process could be performed on a single polyester-cotton blend textile, although such usage may be less efficient.

Once the polyester-cotton blend textiles have been loaded into the rotating hydrolysis reactor, water, a strong base, and optionally a catalyst may be added to the polyester-cotton blend textile to provide a mixture in steps 12, 14 and 16, respectively. The strong base enables the hydrolysis of PET to form the monomer components of terephthalic acid (TPA) and ethylene glycol. The strong base is any suitable base with a pH of 9 or more (e.g., 9.2 or more, 9.5 or more, 9.8 or more, 10 or more, 10.2 or more, 10.5 or more, 10.8 or more, 11 or more, 11.2 or more, 11.5 or more, 11.8 or more, 12 or more, 12.2 or more, 12.5 or more, 12.8 or more, 13 or more, 13.2 or more, 13.5 or more, or 13.8 or more). The upper limit of the pH will be 14. The pH of the strong base can be adjusted as long as the pH is at least 9 or more. In some aspects of the method, the strong base is an alkali metal (Group I of the periodic table) hydroxide, alkaline earth metal (Group II of the periodic table) hydroxide, or ammonium hydroxide. Typically, the strong base will be in the form of an aqueous solution, such as a 10% solution or more (e.g., a 10% solution, 15% solution, a 25% solution, a 40% solution, a 50% solution). In an example, the strong base is a 50% aqueous solution of sodium hydroxide or potassium hydroxide.

The amount of strong base is any effective amount to enable the hydrolysis reaction. In general, the strong base will be used in at least 1% by weight (pbw) (e.g., at least 2 pbw, at least 5 pbw, at least 8 pbw, at least 10 pbw, at least 12 pbw, at least 15 pbw, at least 18 pbw, or at least 20 pbw) of the total liquid composition. Typically, the upper limit of the amount of strong base will be 25 pbw or less (e.g., 20 pbw or less, 18 pbw or less, 15 pbw or less, 10 pbw or less, 8 pbw or less, 5 pbw or less, or 2 pbw or less). Any two of the foregoing endpoints can be used to define a close-ended range, or a single endpoint can be used to define an open-ended range. In an example, the amount of strong base will be 5-15 pbw or 8-12 pbw or about 10 pbw.

If used, the catalyst can comprise a catalyst that enables the PET depolymerization into TPA and ethylene glycol. In some aspects, the catalyst is a phase transfer catalyst. Suitable examples of a phase transfer catalyst include a polymer phase transfer catalyst, such as benzyl trimethylammonium chloride (BTMAC), benzyl triethylammonium chloride (BETEC), benzyl tributylammonium chloride (BTBAC), tetrabutylammonium hydrogen sulfate, methyltributylammonium chloride (MTB AC), tetraethylammonium bromide (TEAB), tetrabutylammonium bromide (TBAB), or a combination thereof. In a preferred aspect, the catalyst comprises benzyl tributylammonium chloride (BTBAC).

The method is designed to operate on a larger scale, including a commercial scale, e.g., on the order of liters (e.g., a 300 L (80 gallon) scale) and kilograms (e.g., a 90 kg (200 lb) scale). In consideration of such end use, the ratio of liquid to textile in the vessel after all the liquid has been added is about 1-5 L: 0.25-2 kg (e.g., 1.9 L: 0.5 kg or 0.5 gal: 1.0 lb).

Once the water, strong base and optional catalyst have been added to the rotating hydrolysis reactor along with the polyester-cotton blend textiles, the resultant mixture may be heated and agitated in the rotating hydrolysis reactor in steps 18 and 20. The mixture should be heated and agitated sufficiently to provide a solution/slurry comprising water, terephthalic acid (TPA), ethylene glycol and other chemicals that can be separated from solid, intact cotton free of PET and the other chemical constituents.

The heating step may be performed at any temperature suitable to enable the depolymerization of polyester terephthalate into TPA and ethylene glycol. The temperature can vary based on the reaction conditions, such as the particular strong base and its concentration and/or catalyst used, if any. For example, the temperature typically will be about 50° C. or more (e.g., 55° C. or more, 60° C. or more, 65° C. or more, 70° C. or more, 75° C. or more, 80° C. or more, 85° C. or more, 90° C. or more, 95° C. or more, 100° C. or more). In some embodiments, the temperature may be between about 90° C. and about 95° C. The upper limit of the heating temperature is not particularly limited but in general is about 200° C. or less (e.g., 190° C. or less, 180° C. or less, 170° C. or less, 160° C. or less, 150° C. or less, 140° C. or less, 130° C. or less, 120° C. or less, 110° C. or less, 100° C. or less, 95° C. or less, or 90° C. or less). Any two of the foregoing endpoints can be used to define a close-ended range, or a single endpoint can be used to define an open-ended range. In an example, the heating step will take place at a temperature at 60° or more, 70° C. or more, 80° C. or more, 60-110° C., 70-100° C., 80-95° C., or about 93° C.

The duration of the heating and agitation of the mixture of blended textiles, water, strong base and catalyst is not particularly limited. In general, the hydrolysis reaction will be at least 20 minutes (e.g., at least 30 min, at least 40 min, at least 60 min, at least 90 min, at least 120 min, at least 150 min, at least 180 min, or at least 210 min). Typically, the hydrolysis reaction will be completed in 240 minutes or less (e.g., 210 min or less, 180 min or less, 150 min or less, 120 min or less, 90 min or less, 60 min or less, 40 min or less, or 30 min or less). Any two of the foregoing endpoints can be used to define a close-ended range, or a single endpoint can be used to define an open-ended range. In an example, the reaction time is about 30-60 minutes, about 40-50 minutes, or about 40 minutes.

Once the hydrolysis reaction is complete, the solution comprising TPA and ethylene glycol and solid reclaimed cotton may be separated in step 22. Advantageously, the cotton/solution separation step may be performed using centrifugation performed using the rotating hydrolysis reactor. Alternatively, the solution can be separated from the solid reclaimed cotton by any suitable solid-liquid separation method. For example, the separating step can be filtration sieving, separating funnel, pumping, centrifugation, or a combination of these steps.

The solid reclaimed cotton can be washed (e.g., with water) as in step 24 and/or dried as in step 26. In some aspects, the solid reclaimed cotton is washed with water to remove any residual base. The resultant reclaimed cotton can be reused in textile applications, such as forming a polyester-cotton blended fabric. If desired, the reclaimed cotton can be re-spun into a yarn. Alternatively, the reclaimed cotton can be used to form regenerated cellulosic fibers, such as viscose or lyocell.

Figure 2:
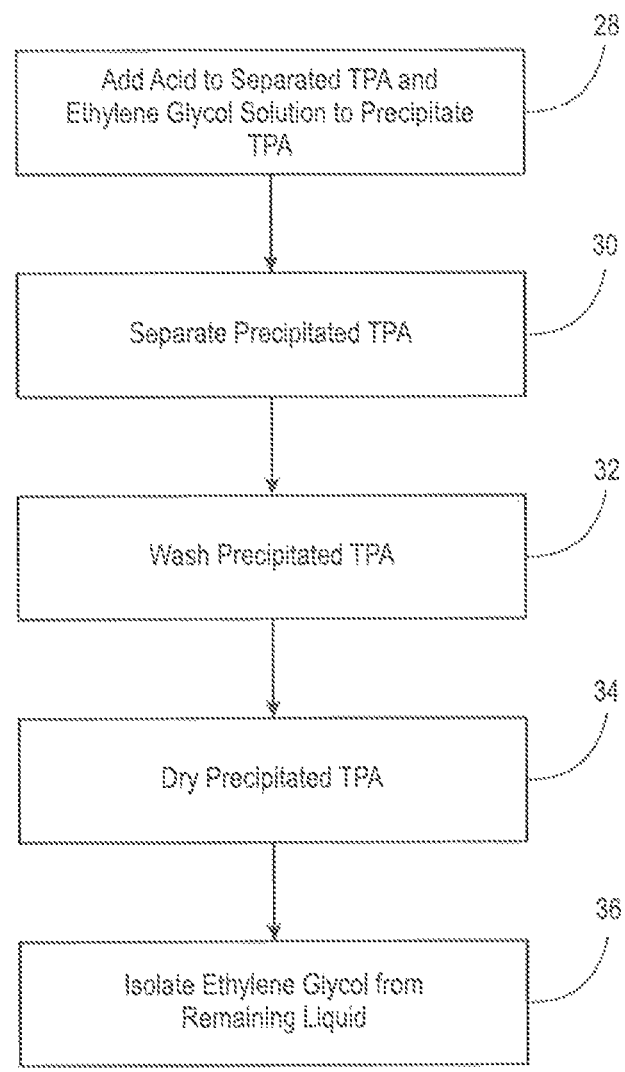
FIG. 2 is a flow diagram showing additional exemplary steps of a process for recycling polyester-cotton blend textile materials according to the present disclosure.

Optionally, the isolated TPA and polyethylene glycol solution may be recovered and further processed to produce additional recycled products such as shown in the flow diagram of FIG. 2. The steps of FIG. 2 can be considered a second phase of the textile recycling process and can be performed using a conventional reactor currently used for processing liquids/chemicals and conventional condensers and dryers already in use in the chemical industry. This second phase may include the step 28 of adding acid to the isolated solution to precipitate TPA. The acid may be any suitable acid that can precipitate the TPA out of solution. In general, the acid will have a pH of about 5 or less (e.g., 4.8 or less, 4.5 or less, 4.2 or less, 4 or less, 3.8 or less, 3.5 or less, 3.2 or less, 3 or less, 2.8 or less, 2.5 or less, or 2.2 or less). The lower limit of the pH will be 1. The pH of the acid can be adjusted as long as the pH is at 5 or less. In an example, the acid will have a pH in the range of 2-5 or 2-3. The acid can be, for example, an inorganic acid or an organic acid. In some aspects, the acid is a mineral acid, such as hydrochloric acid, nitric acid, phosphoric acid, sulfuric acid, boric acid, hydrobromic acid, perchloric acid, hydroiodic acid, or a combination thereof. In a preferred aspect, the mineral acid is hydrochloric acid, sulfuric acid, nitric acid, or a combination thereof. In an especially preferred aspect, the mineral acid is sulfuric acid.

After the TPA has precipitated, the precipitated TPA may be separated in step 30. The precipitated TPA can be washed (e.g., with water) as in step 32 and/or dried as in step 34. In some aspects, the precipitated TPA is washed with water to remove any residual acid. The isolated TPA can be further purified, if desired. For example, the particle size of the isolated TPA can be varied based on the conditions used to isolate and/or purify the TPA. The isolated TPA can be reused, if desired, for polymerization with one or more diols to produce new polyesters.

Optionally, the ethylene glycol can be isolated from the remaining liquid in step 36. The ethylene glycol can be isolated using any suitable method. Typically, the ethylene glycol can be isolated by first distilling the water from the mixture followed by distillation of the ethylene glycol. The ethylene glycol can be further purified and then reused for additional processes, such as polyester formation. In some aspects, the water isolated by distillation is recycled for reuse in the depolymerization method. Once water and ethylene glycol are distilled, some water soluble components of the original hydrolysis reaction can remain. Such water soluble components can include, for example, dyes and cross linkers.

Figure 3:
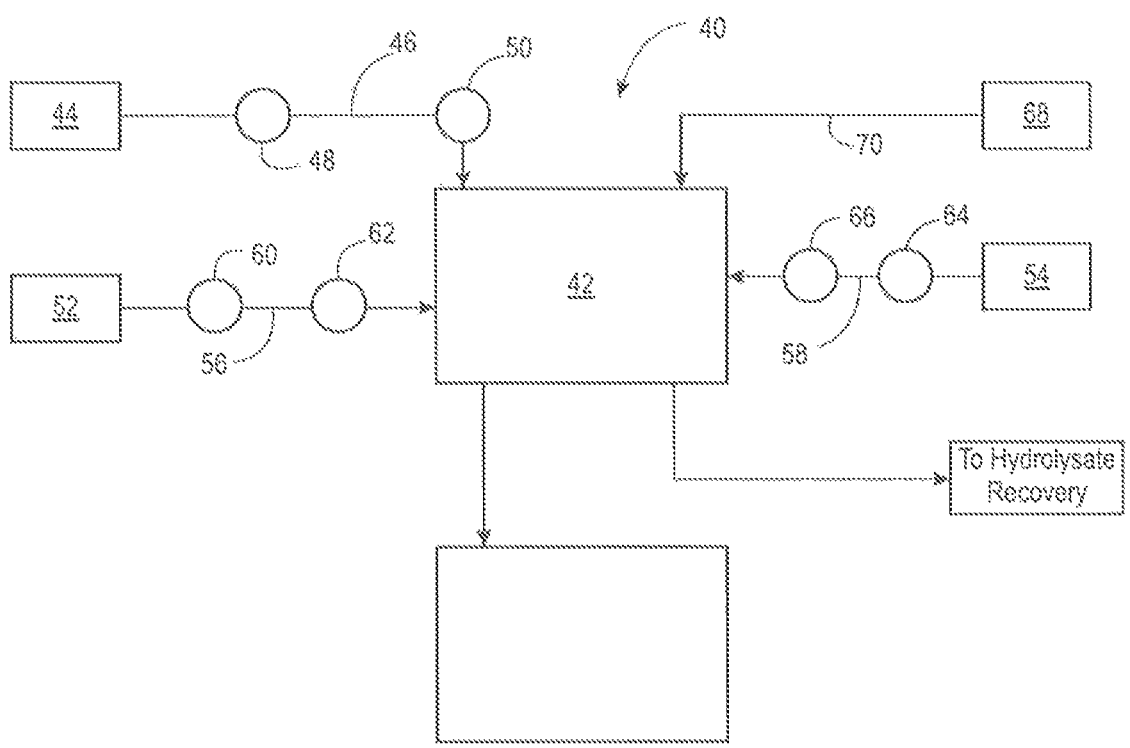
FIG. 3 is a schematic diagram of an illustrative hydrolysis and cotton recovery system of a process for recycling polyester-cotton blend textile materials according to the present disclosure.

Referring to FIG. 3, a hydrolysis and cotton recovery system 40 that is capable of performing the process of FIG. 1 is shown. As discussed above, the system of FIG. 3 includes a rotating hydrolysis reactor 42. To provide water for the hydrolysis reaction, the rotating hydrolysis reactor 42 is connected via suitable a supply line 46 to a water supply 44. The water supply 44 may be a water source that stores water at the desired pressure for the hydrolysis process. Alternatively, a water pump 48 may be provided between the water supply 44 and the rotating hydrolysis reactor 42 as shown in FIG. 3. A water flow meter 50 may also be provided in the water supply line 46 downstream of the water supply 44 to monitor that water is present and/or to monitor the amount of water being added to rotating hydrolysis reactor 42.

For introducing the chemicals necessary for the hydrolysis reaction, the rotating hydrolysis reactor 42 may be in fluid communication with a strong base supply 52 and a liquid catalyst supply 54. In this case, the strong base supply 52 is connected to the rotating hydrolysis reactor 42 by a base supply line 56 and the catalyst supply 54 is connected to the rotating hydrolysis reactor 42 by a catalyst supply line 58. Alternatively, one or both of the chemicals may be added to the rotating hydrolysis reactor 42 by hand. In particular, manual addition of the catalyst may be preferable depending on the scale of the recycling operating and the amount of catalyst being used. In the illustrated embodiment, a base dosing pump 60 and a base flow meter 62 are arranged in the base supply line 56 to allow for monitoring and measurement of the amount of base added to the rotating hydrolysis reactor 42. A catalyst dosing pump 64 and catalyst flow meter 66 are similarly provided in the catalyst supply line 58 to monitor and measure the addition of catalyst to the reactor 42.

A supply of polyester-cotton blend textile waste 68 is also shown schematically in FIG. 3. This supply can take any desirable form, such as a shipping container or other storage vessel. The line 70 connecting the textile waste supply 68 to the rotating hydrolysis reactor 42 represents any suitable method for transporting or delivering the textile waste to the reactor. In one embodiment, overhead slings, which may be part of a sling conveyor system, are used to transport the textile waste to the rotating hydrolysis reactor 42. Other types of conveyor or wheeled cart systems could also be used. However, an overhead sling system may offer particular advantages when recycling high volumes of polyester-cotton blend textile waste.

Figure 4:
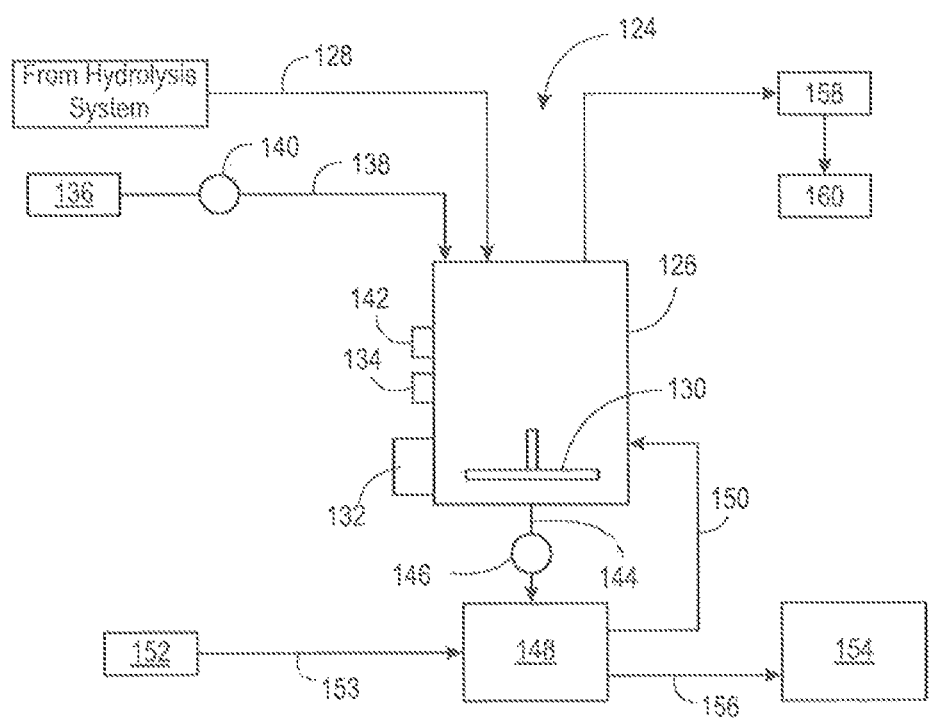
FIG. 4 is a schematic diagram of an illustrative chemical recovery system of a process for recycling polyester-cotton blend textile materials according to the present disclosure.

After completion of the hydrolysis reaction, the solid reclaimed cotton may be transported from the rotating hydrolysis reactor 42 to a dryer 71 while the isolated TPA and ethylene glycol solution is transmitted via line 128 to a hydrolysate recovery system (see FIG. 4). In one embodiment, the dryer 71 can be a conventional gas-fired dryer such as used in commercial laundry facilities. The line 73 in FIG. 3 from the rotating hydrolysis reactor 42 to the dryer 71 is intended to represent any suitable method for transporting the reclaimed cotton to the dryer 71. According to one embodiment, a conveyor system is used to transport the reclaimed cotton to the dryer 71. Other types of transport systems also could be used such as wheeled carts or hoppers.

An exemplary embodiment of the rotating hydrolysis reactor 42 for use in the blended textile recycling process is shown in FIGS. 5-14. In the illustrated embodiment, the hydrolysis reactor 42 includes a reactor housing 72 that in this case is arranged on a support frame 74 (see, e.g., FIG. 6). The illustrated support frame 74 includes a base 76 configured to engage with the ground and a pair of laterally spaced front legs 78 that extend upward from the base 76 to an upper arm assembly 80. To lend further structural support to the support frame 74, a pair of cross braces 82 are provided each of which extends between a lower end of a respective one of the front legs 80 and the upper arm assembly 80. While the illustrated support frame 74 offers certain advantages with respect to the loading and unloading of the hydrolysis reactor in comparison to conventional reactors as described in greater detail below, it should be understood that support frames having other configurations could also be used.

Figure 10:
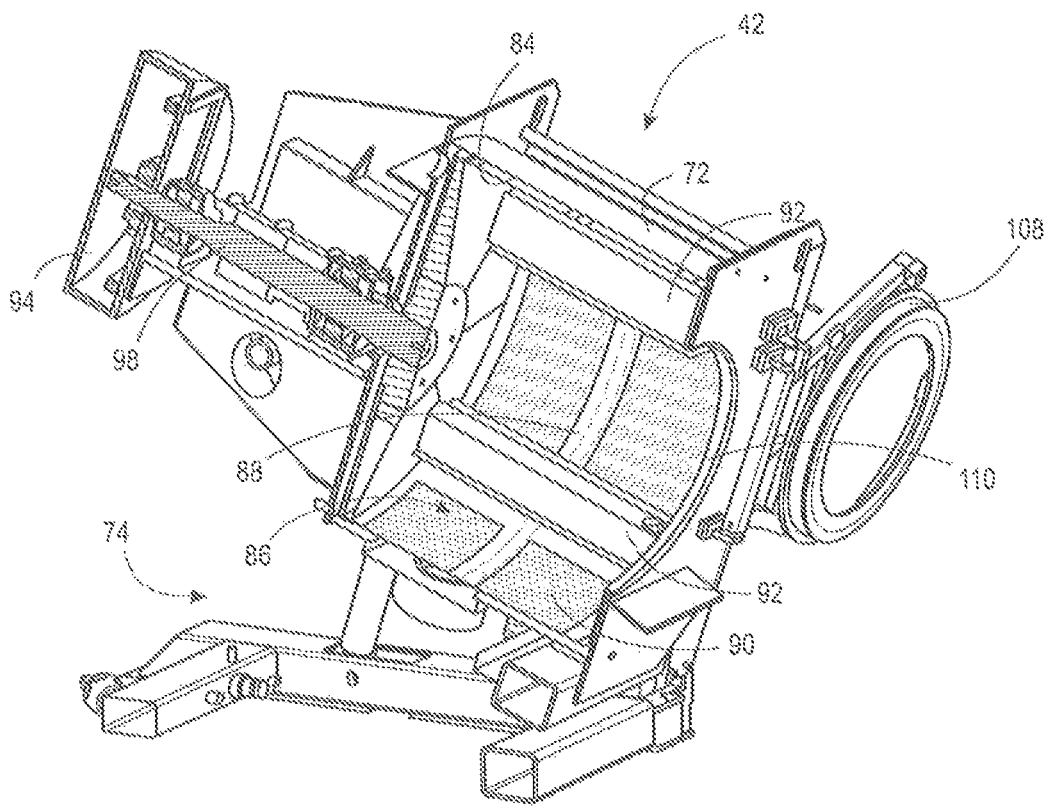
FIG. 10 is a side perspective sectional view of the rotating hydrolysis reactor of FIG. 5, showing the reactor in the unloading position and the front door in the open position.
Figure 11:
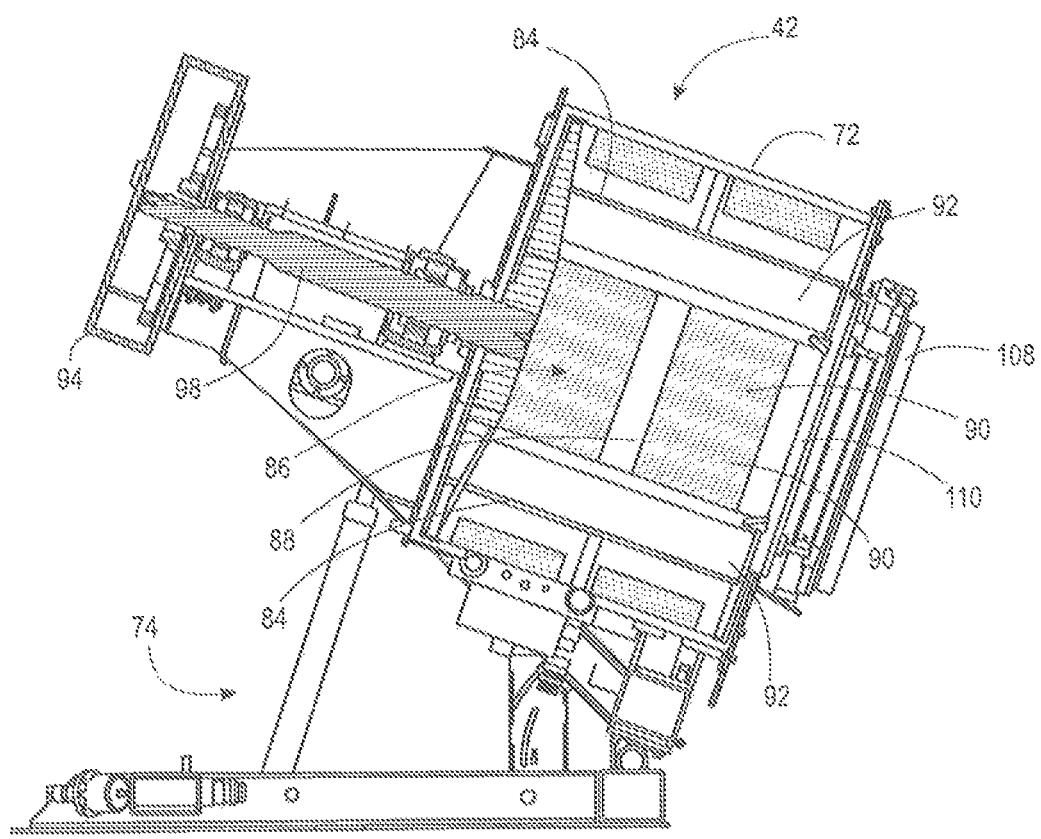
FIG. 11 is a side sectional view of the rotating hydrolysis reactor of FIG. 5, showing the reactor in the unloading position and the front door in the open position.
Figure 12:
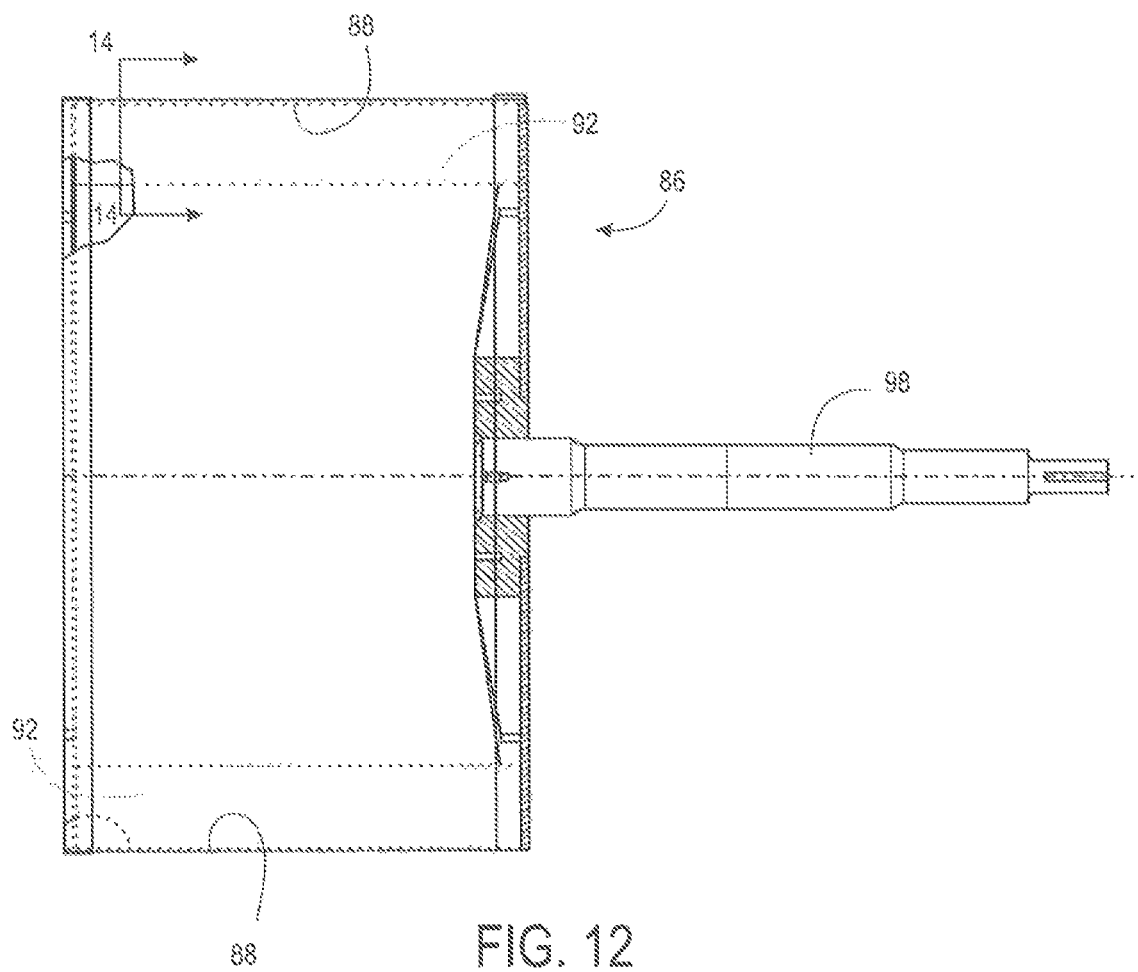
FIG. 12 is a side view of the inner drum of the rotating hydrolysis reactor of FIG. 5.
Figure 13:
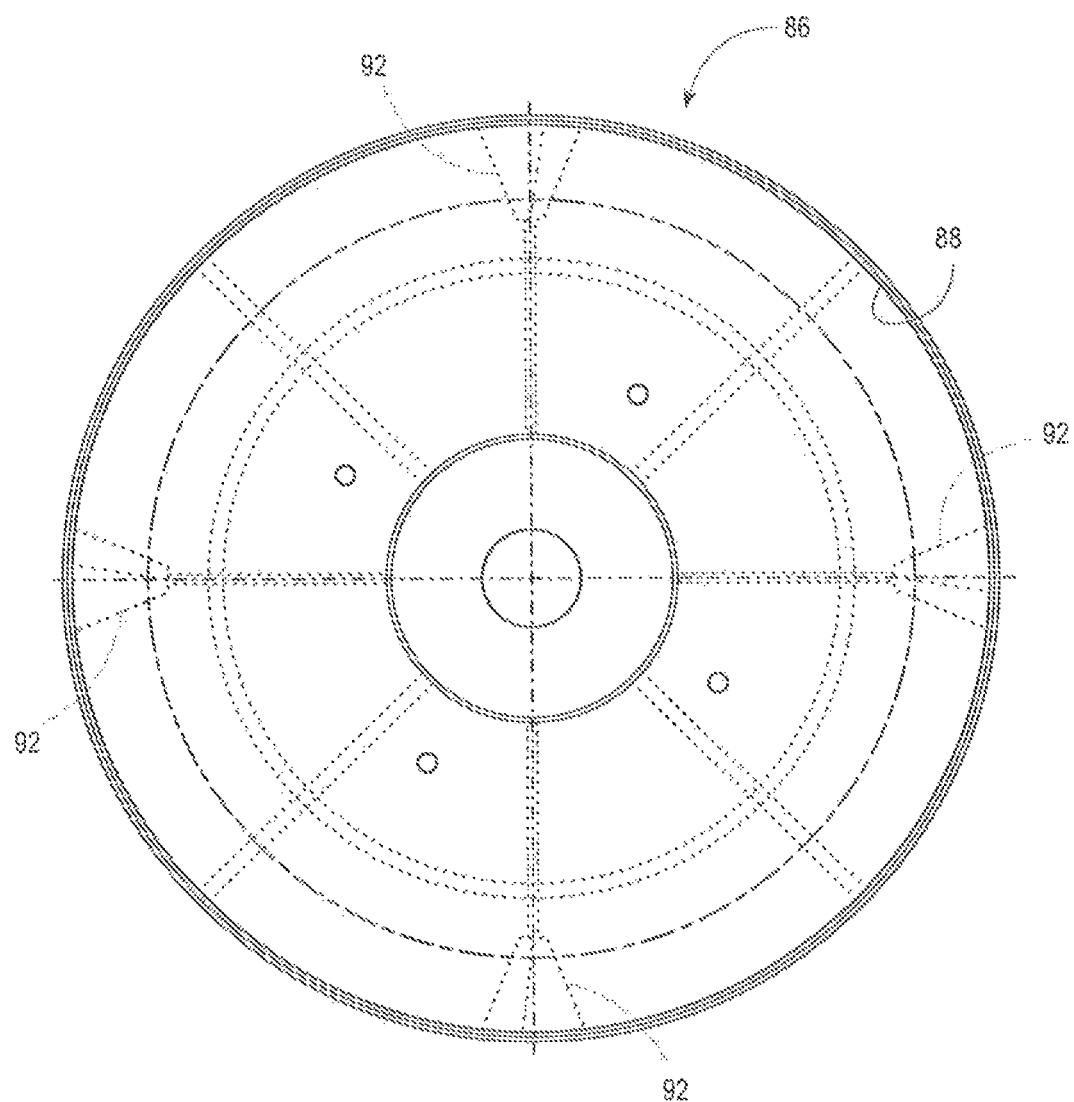
FIG. 13 is an end view of the inner drum of FIG. 12.
Figure 14:
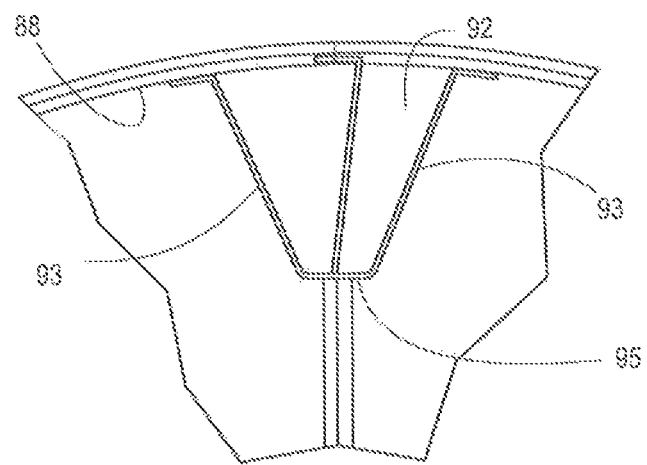
FIG. 14 is a cross-sectional view of the inner drum of FIG. 12 along the line 14-14 of FIG. 12 showing one of the ribs on the interior wall of the inner drum.

For agitating the textile material, water and reaction chemicals during the hydrolysis reaction stage and for extracting the liquid from the recovered cotton during the cotton recovery stage, the reactor housing 72 defines an interior chamber 84 within which an inner drum 86 is supported for rotation relative to the reactor housing 72 as shown in FIGS. 10 and 11. The interior chamber 84 of the reactor housing 72 provides the space for receiving and containing the water and chemicals associated with the depolymerization reaction while the inner drum 86 receives and contains the textile waste material. To allow the water and chemicals in the interior chamber 84 to pass into and out of the inner drum 86, the sidewall 88 of the inner drum 86 is perforated with a plurality of holes 90. As best shown in FIGS. 12-14, the interior of the rotating inner drum 86 may also include a plurality of circumferentially spaced ribs 92 that are arranged on the interior of the sidewall 88 to help agitate the textile waste material, water and chemicals. In the illustrated embodiment, the inner drum 86 is equipped with four ribs 92 (see FIG. 13) that are equally spaced about the circumference of the inner drum 86. As shown in FIG. 14, each rib 92 may be configured with opposing side surfaces 93 that are angled so that they converge towards each other as they extend inward from the sidewall 88 of the inner drum 86. In the illustrated embodiment, each of the side surfaces 93 terminates in a flat end surface 95. Other ribs 92 having other configurations may also be used. The inner drum 86 may have any desired capacity. For example, in one embodiment, the inner drum 86 and reactor housing 72 are configured to have a capacity of up to about 1000 lbs. of textile waste. The reactor housing 72 and inner drum 86 may be made of any appropriate corrosion-resistant material such as, for example, stainless steel.

The use of a rotating inner drum 86 with ribs 92 offers several advantages as compared to conventional hydrolysis reactors. For example, the mechanical agitation produced by the rotating inner drum 86 and ribs 92 allows for an effective polymerization reaction with the use of less water and reaction chemicals. This allows the process to operate more much efficiently at higher volumes and in a more energy-efficient and cost-effective manner. In some embodiments, the disclosed rotary hydrolysis reactor can allow for the use of up to twelve times less water than conventional reactors. The disclosed rotary hydrolysis reactor also allows the individual pieces of textile waste to be relatively larger in size than conventional reactors which often can require the textile waste to be shredded prior to being added to the reactor in order to achieve sufficient agitation. The inner drum 86 with ribs 92 arrangement also contributes to the recovery of high quality cotton fibers that can be used in a greater variety of high-value products. Additionally, the mechanical agitation provided by the rotating inner drum 86 and ribs 92 not only facilitates the depolymerization reaction but also helps mechanically remove non-polyester components of the textile waste, such as zippers, buttons, labels, and/or decorative elements. The inner drum 86 and rib 92 arrangement is also much easier to clean than agitators used in conventional hydrolysis reactors, which substantially reduces manufacturing downtime and maintenance costs.

Figure 6:
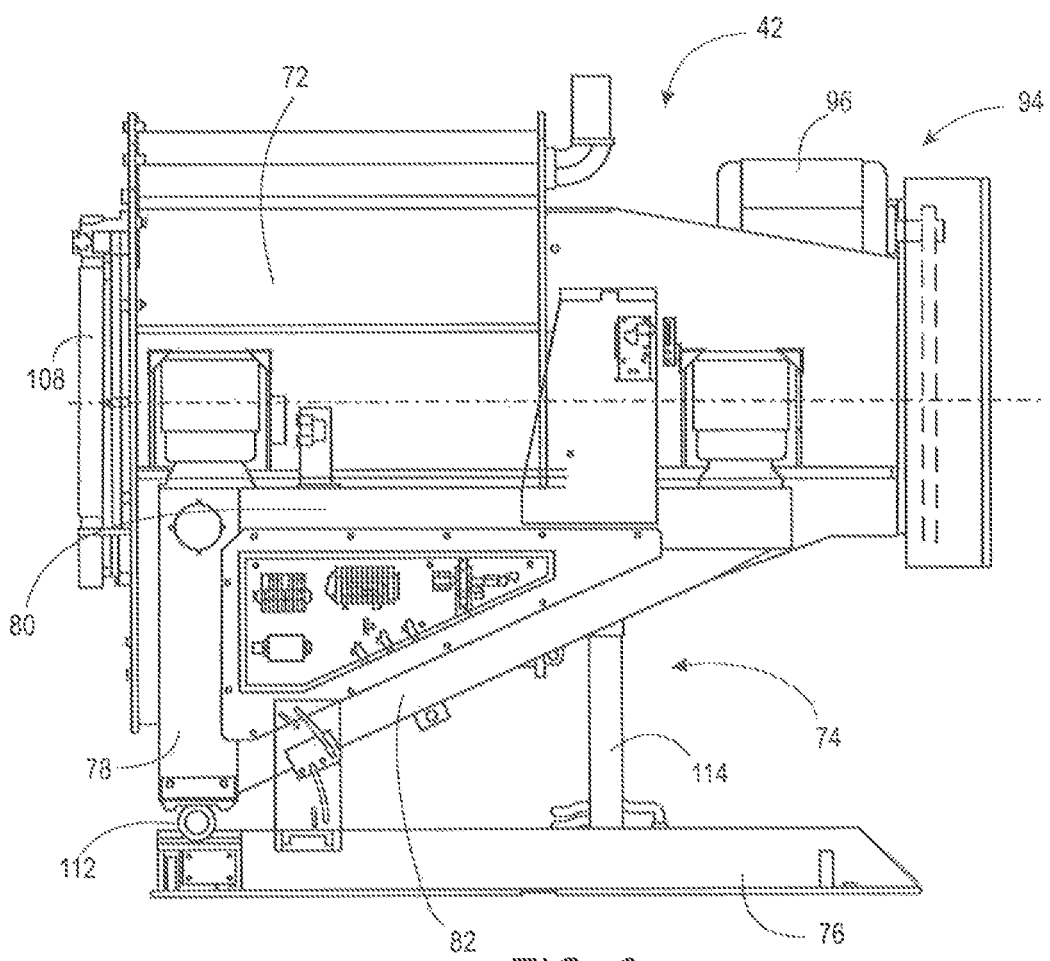
FIG. 6 is a side view of the rotating hydrolysis reactor of FIG. 5.

For driving rotation of the inner drum 86 relative to the reactor housing 72, the illustrated reactor 42 includes a rotary drive assembly 94 that in this case includes an electric motor 96 that is operatively connected to a drive shaft 98 of the inner drum 86 (see, e.g., FIGS. 6, 10 and 11). The arrangement of the drive shaft 98 and the inner drum 86 can also be seen in FIG. 12. The rotary drive assembly 94 may be configured to rotate the inner drum 86 relative to the reactor housing 72 at different speeds depending on the stage of the hydrolysis process. For instance, during the depolymerization reaction the inner drum 86 may rotate relative the reactor housing 72 in a manner that optimizes agitation of the textile waste material, the water and the reaction chemicals. Then, during the separation step, the inner drum 86 may rotate at a higher speed to produce sufficient centrifugal force to drive the liquid TPA and ethylene glycol solution out of the solid reclaimed cotton. This centrifugally separated liquid exits the inner drum 86 through the perforations in the sidewall 88 of the inner drum 86. The separated liquid is then collected in the reactor housing 72 and removed from the rotary hydrolysis reactor 42 via an internal drain pump provided in the reactor. According to one embodiment, the inner drum 86 and drive assembly 94 are configured such that the inner drum 86 can rotate at speeds of up to about 500 rpm.

Figure 9:
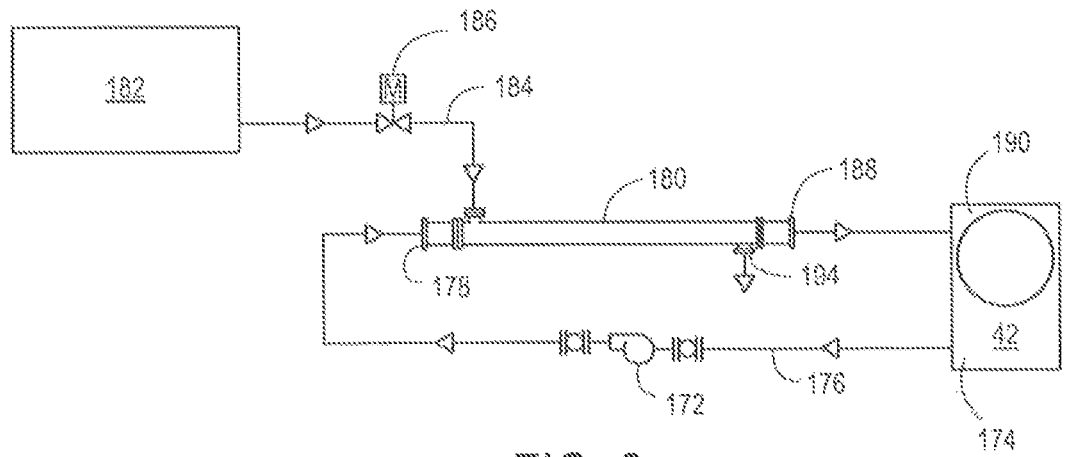
FIG. 9 is a schematic diagram of an illustrative slurry heating system for the rotating hydrolysis reactor of FIG. 5.

For maintaining the water and chemicals at the desired temperature for the hydrolysis reaction, the rotating hydrolysis reactor 42 may be equipped with a slurry heating system 170. One embodiment of an appropriate slurry heating system 170 is shown in FIG. 9. The slurry heating system 170 of FIG. 9 uses a pump 172 to draw the water and chemical slurry out of a bottom portion 174 of the rotating hydrolysis reactor 42 through an outlet line 176. The outlet line 176 directs the slurry to an inlet end 178 of a heat exchanger 180 which operates to heat the slurry to the desired temperature for the hydrolysis reaction. In this case, the heat exchanger 180 is heated via a steam generator 182. Steam from the steam generator 182 is directed to the heat exchanger 180 through a steam supply line 184 and can be controlled by a steam control valve 186. Once heated, the heated slurry exits the heat exchanger 180 at an outlet end 188 thereof and is directed back to an upper portion 190 of the rotating hydrolysis reactor 42 via a slurry inlet line 192. Cooled condensate exits the heat exchanger 180 via a condensate outlet 194. In operation, the slurry heating system 170 draws cooled slurry from the bottom portion 174 of the reactor 42, heats the slurry to the desired temperature and then reintroduces the hot slurry into the upper portion 190 of the reactor 42. The slurry heating system 170 may be controlled to maintain the slurry in the reactor at a desired temperature. While a steam heat exchanger arrangement is shown, it should be understood that the heating can be performed using equipment other than a steam heat exchanger.

Figure 5:
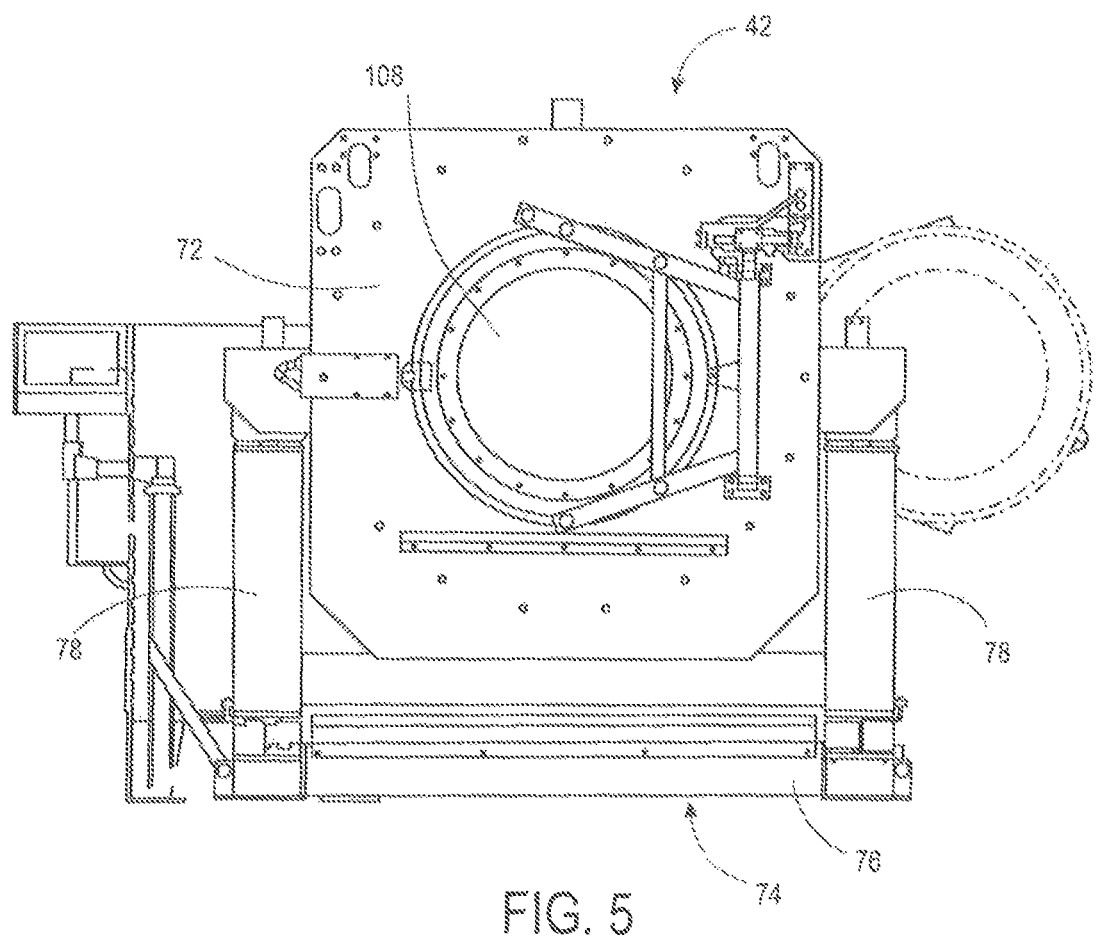
FIG. 5 is a front view of an exemplary rotating hydrolysis reactor for use in the polyester-cotton blend textile recycling process according to the present disclosure.

To permit the polyester-cotton blend textile waste to be loaded into the inner drum 86, the rotary hydrolysis reactor 42 illustrated in FIGS. 5-8, 10 and 11 includes a movable outer door 108. More specifically, the outer door 108 is pivotably connected to the reactor housing 72 to move between open and closed positions relative to a door opening 110 in the wall of the reactor housing 72. In the open position, the door opening 110 in the reactor housing 72 is accessible for the loading and unloading of the textile waste material into and out of the inner drum 86 (see, e.g., FIG. 10). In the closed position (see, e.g, FIG. 5), the outer door 108 closes off the door opening 110 in the reactor housing 72 so that the depolymerization hydrolysis reaction can take place safely and effectively. In this case, as shown in FIG. 5, the outer door 108 is hinged to the side so that the outer door 108 pivots laterally between the open and closed positions, although other door pivot arrangements may be used. To ensure the outer door 108 maintains a tight seal with the door opening 110 in the reactor housing 72, a seal assembly may be provided on the perimeter of one or both of the outer door 108 and the door opening 110. The seal assembly may be particularly designed for use with the chemicals used in the depolymerization process.

Figure 7:
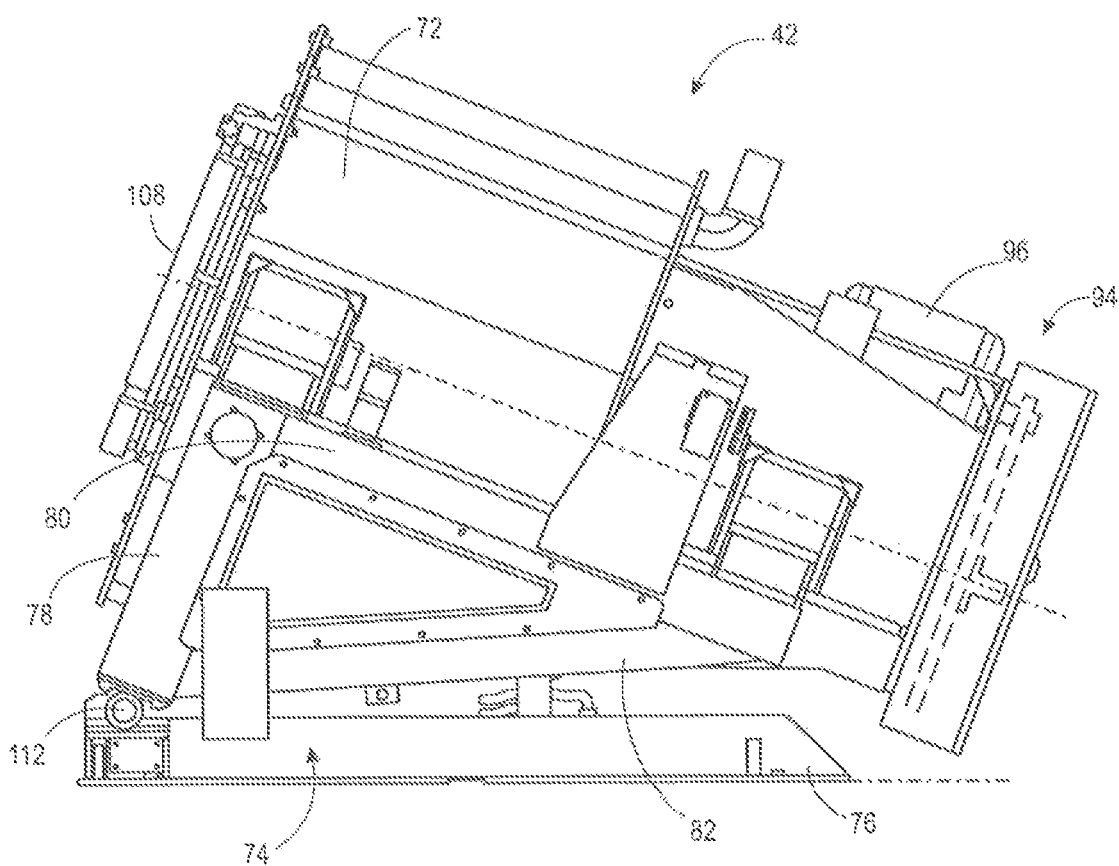
FIG. 7 is a side view of the rotating hydrolysis reactor of FIG. 5 showing the reactor in a loading position.
Figure 8:
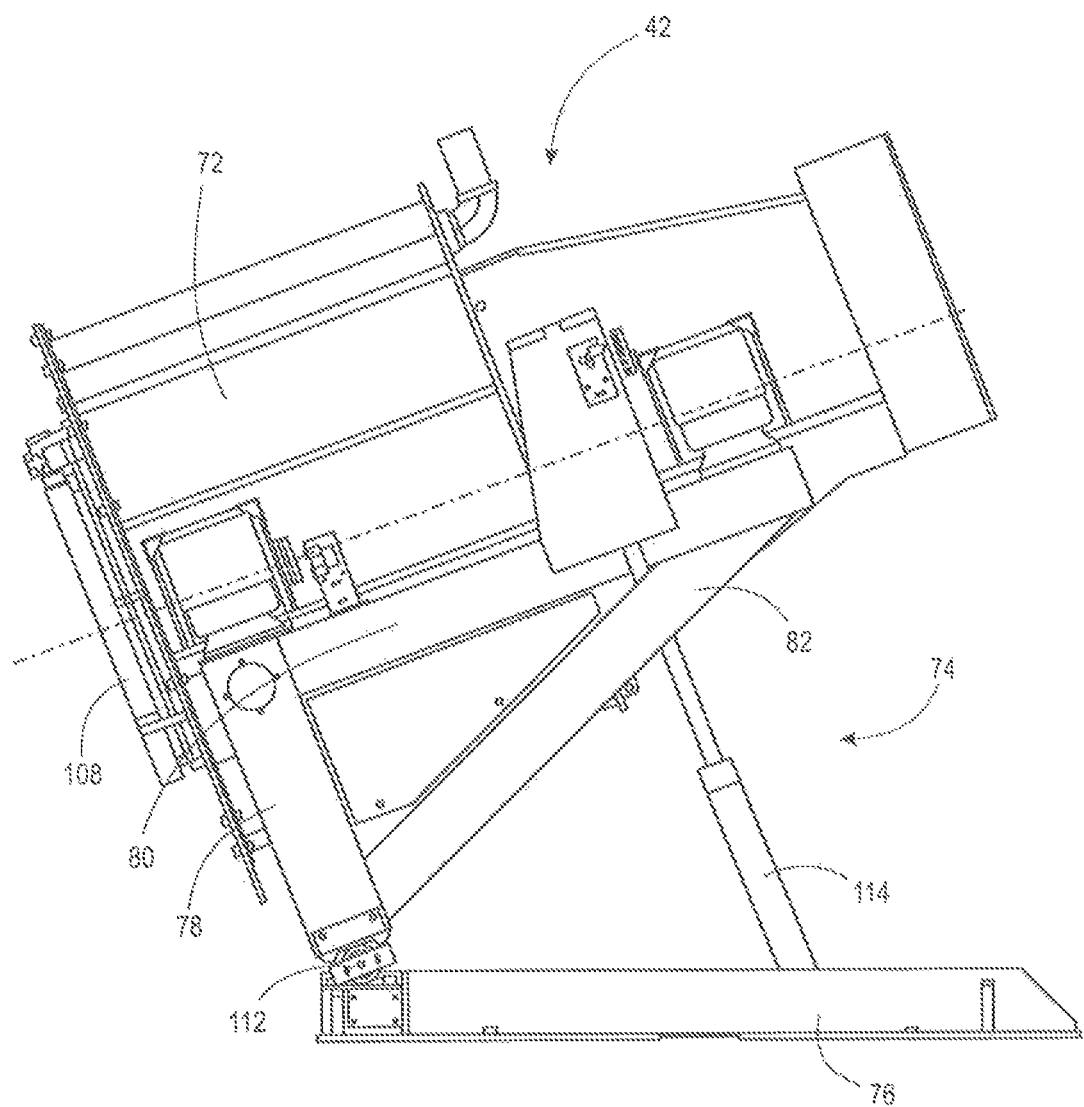
FIG. 8 is a side view of the rotating hydrolysis reactor of FIG. 5 showing the reactor in an unloading position.

To further facilitate loading of the textile waste into the inner drum 86, the reactor support frame 74 may be configured such that the front end of the reactor housing 72 can tilt upwardly from a normal horizontally-oriented operating position (shown, for example, in FIG. 6) to a loading position as shown in FIG. 7. This upwardly tilted load position is particularly useful when loading the reactor 42 via overhead slings. To further facilitate unloading of the reclaimed solid cotton from the inner drum 86 at the conclusion of the hydrolysis process, the reactor support frame 74 may be configured such that the front end of the reactor housing 72 can tilt downward from the normal horizontally-oriented operating position to an unloading position as shown in FIG. 8. This downwardly tilted unload position is particularly useful when the reclaimed cotton is unloaded onto a belt conveyor for transport, for example, to the dryer 71. In the illustrated embodiment, as shown in FIGS. 6-8, the movement between the loading, operating and unloading positions is enabled by a pivotable connection 112 of the front legs 78 of the support frame 74 to the base 76 of the support frame. For pivoting the front legs 78 relative to the base 76, at least one tilt actuator 114 may be provided between the reactor housing 72 and the base 76 of the support frame 74. The tilt actuator 114 in this case is configured such that extension and retraction of the actuator pivots the legs 78 relative to the base 76 and thereby moves the reactor housing 72 between the various positions.

Figure 15:
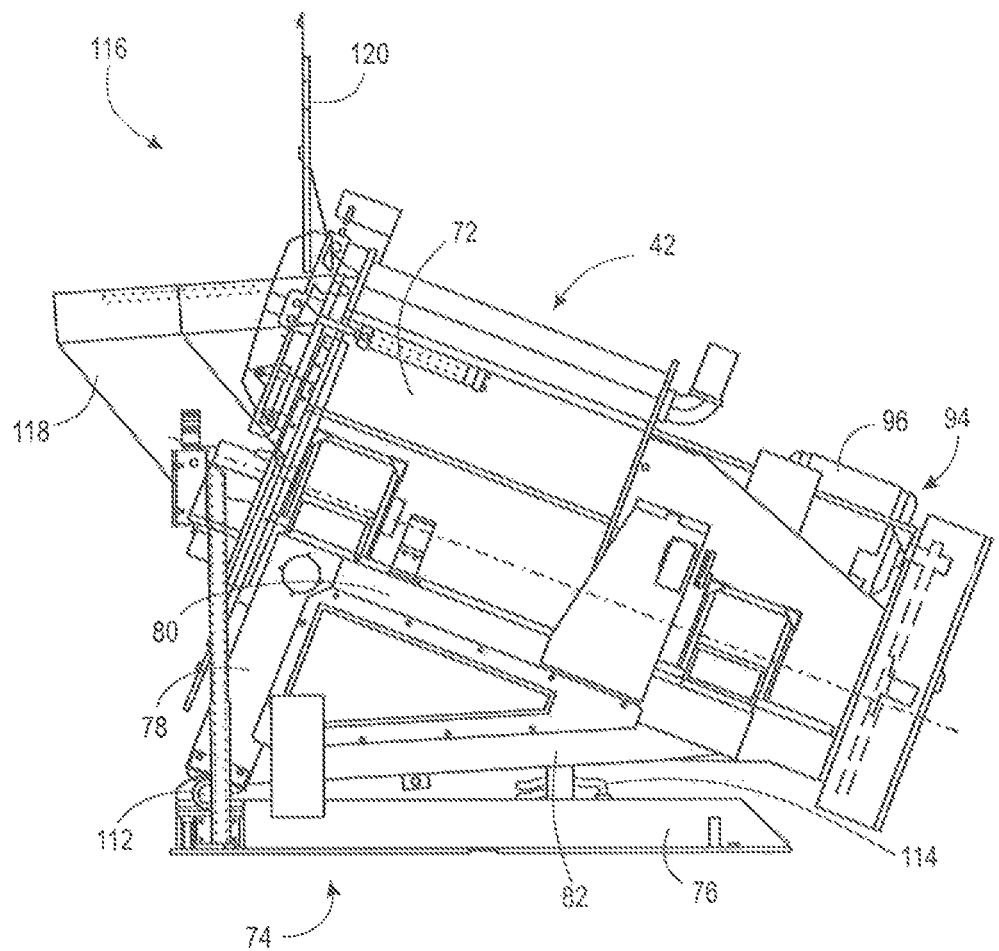
FIG. 15 is a side view of the rotating hydrolysis reactor of FIG. 5 equipped with a hopper assembly instead of a front door and showing the hopper in the lowered position.
Figure 16:
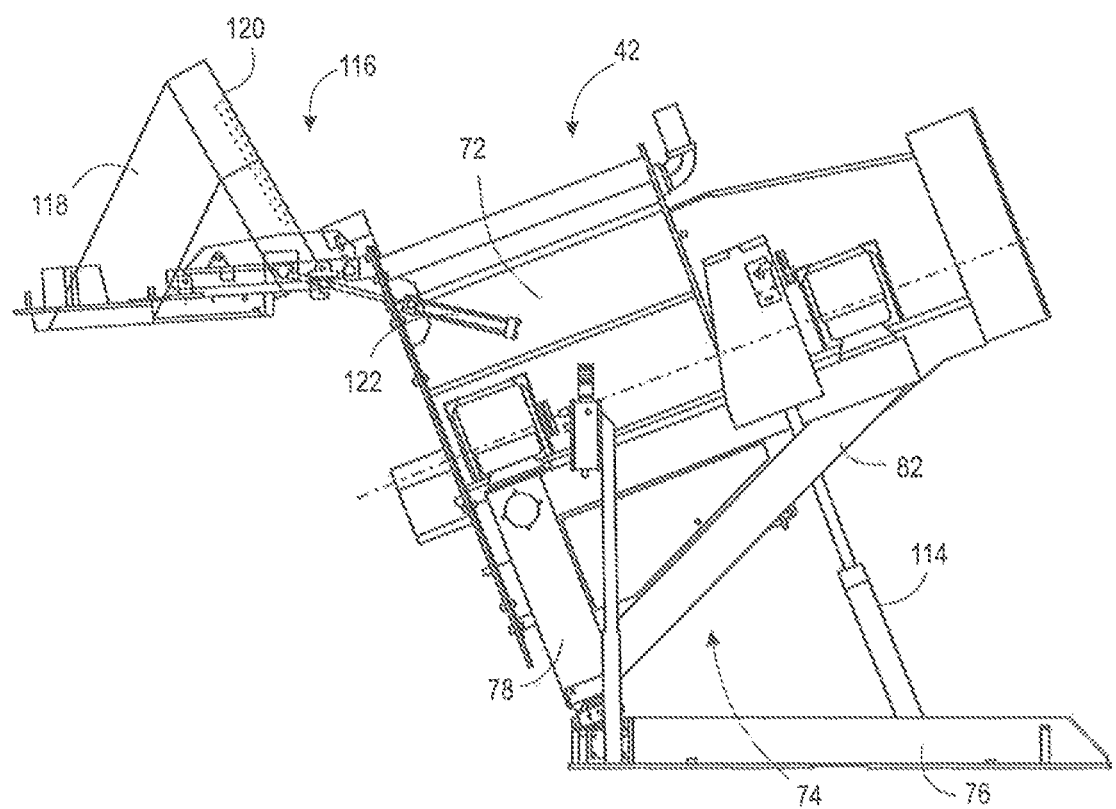
FIG. 16 is a side view of the rotating hydrolysis reactor of FIG. 9 showing the front hopper in the raised position.

As an alternative to a hinged outer door, to ease loading of textile waste into the inner drum 86 particularly from overhead slings, the rotating hydrolysis reactor 42 may be equipped with a hopper assembly 116 as shown in FIGS. 15 and 16. More specifically, the hopper assembly 116 may be mounted on the front side of the reactor housing 72 in overlying relation to the front opening 110 of the reactor housing 72. The hopper assembly 116 includes in this case an upwardly opening chute 118 with a hopper door 120 at the upper end of chute 118 that is movable between open and closed positions. In the lowered closed position shown in FIG. 16, the hopper door 120 blocks off the upper end of the chute 118. This closed position of the chute door 120 is used both in the unloading position of the reactor 42 (shown in FIG. 16) and in the operating position of the reactor 42 in which the hopper door 120 seals the rotating hydrolysis reactor 42 so that the depolymerization process can be performed. In the raised open position of the hopper door as shown in FIG. 15, the open upper end of the chute 118 is unobstructed for loading of textile materials into the chute 118 which directs the textile materials into the inner drum 86 through the door opening in the reactor housing 72. A door actuator may be provided that pivots the hopper door between the open and closed positions.

To allow for unloading of the recovered cotton from the inner drum, the hopper assembly 116 may be supported on the reactor housing 72 for movement between lowered and raised positions. In the lowered position, the chute 118 is arranged adjacent the front face of the reactor housing 72. In this position, the chute 118 can be used for loading the rotating hydrolysis reactor when the reactor housing 72 is in the loading position (see FIG. 15). The lowered position of the chute is the position that is used during operation of the reactor. In the raised position, the hopper chute 118 is pivoted upward relative to the reactor housing 42 and away from the opening in the reactor housing as shown in FIG. 16. This raised position enables unloading of the rotating hydrolysis reactor 42 following a hydrolysis cycle without interference from the hopper assembly 116. The movement of the hopper assembly 116 between the raised and lowered positions may be driven by one or more hopper tilt actuators 122 (see FIG. 16).

The ability to move the reactor between loading and unloading positions allows the rotating hydrolysis reactor to work with high volume conveyance systems during both loading and unloading and thereby allows the reactor to efficiently process very high volumes of textile waste, particularly as compared to conventional hydrolysis reactors. Moreover, this arrangement allows the high volume of material to be loaded and unloaded quickly and easily with a minimal amount of labor. A hopper assembly can further facilitate loading of the reactor in certain applications. Thus, the rotating reactor housing provides a hydrolysis process that can be scaled easily and affordably to recycle high volumes of textile waste.

Referring to FIG. 4, there is shown a system for recovery of the TPA and ethylene glycol from the liquid solution that is separated from the solid reclaimed cotton after the hydrolysis reaction is complete according to the method of FIG. 2. In the illustrated embodiment, the recovery system 124 includes a recovery vessel 126 that is configured to receive the liquid hydrolysate from the rotating hydrolysis reactor 42. The liquid hydrolysate may be directed from the rotating hydrolysis reactor 42 via line 128 as shown in FIG. 4. To maintain a well-mixed solution during processing, the recovery vessel 126 may be equipped with an appropriate agitator 130. The recovery vessel 126 may also be provided with a heating system 132, which can be used as desired to heat the contents of the recovery vessel. To monitor the temperature of the contents of the recovery vessel 126, a temperature sensor 134 also may be provided.

An acid supply 136 is also in communication with the recovery vessel 126 via line 138. An acid dosing pump 140 may be provided in the line 138 to control delivery of the acid to the recovery vessel 126. Additionally, a pH meter 142 may be provided on the recovery vessel 126 to monitor the pH of the solution in the recovery vessel 126 as the acid is added and thereby detect when the pH of the solution in the recovery vessel 126 drops to the point at which the TPA will precipitate from the hydrolysate solution.

Once the pH in the recovery vessel 126 has reached the desired level, the hydrolysate in the recovery vessel 126 may be directed, such as via line 144 and recovery vessel pump 146, to and through a TPA recovery filter 148. The TPA recovery filter 148 may be configured to entrap the TPA precipitate as the hydrolysate passes through the filter. After passing through the filter, the remaining liquid can then be recirculated via a recirculation line 150 back to the recovery vessel 126. The hydrolysate can circulate through the recovery vessel 126 and the TPA recovery filter 148 until substantially all of the TPA precipitate has been removed. In the illustrated embodiment, the TPA recovery filter 148 may be in communication with a water supply 152 via a water supply line 153 to wash the filter cake in the TPA recovery filter 148 once the precipitated TPA separation has been completed. To facilitate this washing step, the TPA recovery filter 148 may have inlet and outlet valves that are arranged such that when closed the valves isolate the TPA recovery filter 148 from the rest of the system when water is being directed to the filter. The washed TPA precipitate may then be transported to a dryer 154. This transportation is referenced schematically by the line 156 in FIG. 4 and is meant to reference any method of transportation to the dryer 154 including transporting the TPA precipitate by hand.

Once the TPA precipitate has been separated, the recovery vessel 126 may begin to heat the remaining contents to prepare to distill the water from the ethylene glycol and then, subsequently, the ethylene glycol from the residual salts and compounds. The agitator 130 in the recovery vessel may continue to operate during the distillation process. Once the water in the hydrolysate in the recovery vessel 126 has been boiled off, the temperature in the recovery vessel may be raised to the boiling point of the ethylene glycol in order to separate the ethylene glycol from the salts and other impurities. The ethylene glycol vapors are then directed to a glycol recovery condenser 158. The glycol recovery condenser 158 can be cooled via any suitable means, such as recirculation of a cooling fluid. Once condensed, the ethylene glycol can be directed from the condenser 158 to an appropriate storage vessel 160.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for processing polyester-cotton blend textile waste, comprising:
    adding polyester-cotton blend textile waste to a rotating drum of a rotary hydrolysis reactor, wherein the rotating drum has a plurality of ribs arranged on an inner surface of the rotating drum;
    adding water and a base to the rotary hydrolysis reactor;
    heating the water and base added to the rotary hydrolysis reactor;
    hydrolyzing PET in the polyester-cotton blend textile waste into a TPA and ethylene glycol solution and solid reclaimed cotton free of PET by agitating the heated water, base and polyester-cotton blend textile waste with the plurality of ribs by rotating the inner drum relative to a housing of the rotary hydrolysis reactor;
    separating through centrifugation the TPA and ethylene glycol solution from the solid reclaimed cotton by rotating the inner drum relative to the housing of the rotating hydrolysis reactor;
    directing the separated TPA and ethylene glycol solution to a hydrolysate recovery vessel:
    adding acid to the separated TPA and ethylene glycol solution in the hydrolysate recovery vessel to precipitate TPA;
    separating the precipitated TPA from remaining liquid in the hydrolysate recovery vessel; and
    isolating ethylene glycol from remaining liquid in the hydrolysate recovery vessel.

2. The method according to claim 1 wherein the base has a pH of 9 or more.

3. The method according to claim 2 wherein the base comprises a 10% or more aqueous solution.

4. The method according to claim 1 further including the step of adding a catalyst to the rotary hydrolysis reactor.

5. The method according to claim 4 wherein the catalyst is a phase transfer catalyst.

6. The method according to claim 1 wherein after the water and base have been added the ratio of liquid to textile waste in the basis is 1-5 L liquid:0.25-2 kg textile waste.

7. The method according to claim 1 wherein the water and base in the rotary hydrolysis reactor are heated to about 50° C. or more.

8. The method according to claim 1 wherein the water and base in the rotary hydrolysis reactor are heated to between about 90° C. and about 95° C.

9. The method according to claim 1 wherein the hydrolysis reaction is completed in 60 minutes or less.

10. The method according to claim 1 further including the step of washing the solid reclaimed cotton.

11. The method according to claim 1 wherein the acid has a pH of about 3 or less.

12. The method according to claim 1 further including the step of washing the precipitated TPA.

13. The method according to claim 1 wherein during the separation of TPA and ethylene glycol from the solid reclaimed cotton step the rotating drum rotates at a relatively higher speed than during the agitating step.

14. A rotating hydrolysis reactor for processing polyester-cotton blend textile waste comprising:
    a reactor housing defining an interior chamber for receiving a water and chemical slurry associated with the hydrolysis reaction;
    an inner drum supported in the interior chamber for rotation relative to the reactor housing and for receiving polyester-cotton blend textile waste, the inner drum including a sidewall that is perforated with a plurality of holes;
    a plurality of spaced apart ribs supported on an interior surface of the sidewall of the inner drum for agitating the polyester-cotton blend textile waste when the inner drum is rotated relative to the reactor housing;
    a slurry heating system including a slurry outlet line in communication with the interior chamber of the reactor housing for drawing the water and chemical slurry out a bottom portion of the reactor housing, the slurry outlet line directing the water and chemical slurry to a heat exchanger, the heat exchanger being operable to heat the water and chemical slurry to a desired temperature, the slurry heating system further including a slurry inlet line that communicates with the reactor housing and is configured to direct heated water and chemical slurry from the heat exchanger back into the interior chamber of the reactor housing.

15. The rotating hydrolysis reactor of claim 14 further including a rotary drive assembly for rotating the inner drum relative to the reactor housing at a variable speed.

16. The rotating hydrolysis reactor of claim 14 wherein the reactor housing is supported on a support frame that is configured to tilt the reactor housing between a loading position, an operating position and an unloading position.

17. The rotating hydrolysis reactor of claim 14 further including a hopper assembly arranged on a front side of the reactor housing in overlying relation to a front opening in the reactor housing and wherein the hopper assembly includes a chute with a hopper door at an upper end of the chute.

18. A system for processing polyester-cotton blend textile waste comprising:
    a rotating hydrolysis reactor comprising:
        a reactor housing defining an interior chamber for receiving a water and chemical slurry associated with the hydrolysis reaction;
        an inner drum supported in the interior chamber for rotation relative to the reactor housing and for receiving polyester-cotton blend textile waste, the inner drum including a sidewall that is perforated with a plurality of holes;
        a plurality of spaced apart ribs supported on an interior surface of the sidewall of the inner drum for agitating the polyester-cotton blend textile waste when the inner drum is rotated relative to the reactor housing; and
    a hydrolysate recovery system configured to receive liquid hydrolysate from the rotating hydrolysis reactor comprising:
        a recovery vessel configured to receive liquid hydrolysate from the rotating hydrolysis reactor, the recovery system including an agitator and a heating system;
        an acid supply system for directing acid to the recovery vessel;
        a TPA recovery filter configured to capture TPA precipitate as liquid hydrolysate from the recovery vessel is directed through the TPA recovery filter; and a glycol recovery condenser in communication with the recovery vessel for receiving and condensing into liquid ethylene glycol vapors from the recovery vessel.

19. The system of claim 18 wherein the rotating hydrolysis reactor includes a slurry heating system including a slurry outlet line in communication with the interior chamber of the reactor housing for drawing the water and chemical slurry out a bottom portion of the reactor housing, the slurry outlet line directing the water and chemical slurry to a heat exchanger, the heat exchanger being operable to heat the water and chemical slurry to a desired temperature, the slurry heating system further including a slurry inlet line that communicates with the reactor housing and is configured to direct heated water and chemical slurry from the heat exchanger back into the interior chamber of the reactor housing.

20. The system of claim 19 further including a recirculation line that directs a remaining liquid portion back to the recovery vessel after passing through the TPA recovery filter.

* * * * *